United States Patent [19]
Dreyer et al.

[11] Patent Number: 5,354,946
[45] Date of Patent: Oct. 11, 1994

[54] **GENE COMPLEX PARTICULARLY USEFUL FOR MODIFYING PLANTS SUCH AS *CUCUMIS MELO* AND *CUCUMIS MELO* INCORPORATING SAID GENE COMPLEX**

[75] Inventors: Alain Dreyer, Chateauneuf de Gadagne; Jean-Paul Ginoux, Eyragues, both of France

[73] Assignee: Bio-Obtention SC, Montferrier, France

[21] Appl. No.: 103,305

[22] Filed: Aug. 6, 1993

Related U.S. Application Data

[63] Continuation of Ser. No. 842,375, Mar. 27, 1992, abandoned.

[30] Foreign Application Priority Data

Jul. 27, 1990 [FR] France .................. 90 09622

[51] Int. Cl.$^5$ .......................... A01H 5/00; A01H 1/04
[52] U.S. Cl. ..................... 800/230; 800/200; 800/220; 800/DIG. 19
[58] Field of Search ............... 800/200, 205, 220, 230, 800/DIG. 18–21; 435/240.47, 240.51

[56] References Cited

PUBLICATIONS

Kaldewey et al., Hormonal Regulation in Plant Growth and Development, Proc. Advanced Study Institute, Izmir (1971) p. 247.
Gardner et al, Physiology of Crop Plants, Iowa State University Press, pp. 180–181.
Leopold, A., Plant Growth and Development, McGraw Hill Co. (1964) p. 291.
Ray et al., Botany, Dryden Press (1983) pp. 297–299.
Pratt, H., Melons, pp. 207–233, The Biochemistry of Fruits and their Products, Hulme, A. C. (Ed.), vol. 2 (1971).
Kendall, S. A. et al. 1988 Genetic variation of ethylene production in harvested muskmelon fruits. Hort Science 23:759–761.
Brady, C. J. 1987 Fruit ripening. Ann Rev Plant Physiol 38:155–178.
Yang, S. F. et al. 1984 Ethylene biosynthesis and its regulation in higher plants. Ann Rev Plant Physiol 35:155–189.
Hamilton, A. J. et al. 1990 Antisense gene that inhibits synthesis of the hormone ethylene intransgenic plants. Nature 346:284–287.

*Primary Examiner*—David T. Fox
*Assistant Examiner*—Bruce R. Campbell
*Attorney, Agent, or Firm*—Jacobson, Price, Holman & Stern

[57] ABSTRACT

*Cucumis melo* (melon) line 95LS444. Fruits of line 95LS444 release ethylene at a constant rate for eight days after reaching maximum ethylene release, and remain firm textured for a longer period after harvest than other melon varieties.

3 Claims, 3 Drawing Sheets

GENE COMPLEX PARTICULARLY USEFUL FOR MODIFYING PLANTS SUCH AS CUCUMIS MELO AND CUCUMIS MELO INCORPORATING SAID GENE COMPLEX

This is a continuation of application Ser. No. 7/842,375, filed Mar. 27, 1992, now abandoned.

The present invention relates to a novel gene complex particularly useful for modifying plants, particularly Cucumis melo.

In the fruits sector, the key stage for products which have to be marketed is that of maturation. Maturation is a sequence of events which begins generally after growth of the fruit has ceased and which should result in optimal overall quality for consumption, particularly with respect to the organoleptic qualities.

If the fruit exceeds this mature stage, cellular disorganization ensues which corresponds to what is known as overmaturation. This overmaturation corresponds, for certain fruits, to the end of a paroxysm of ethylene production.

Accordingly, fruits are divided into two groups taking account of their behavior with respect to ethylene:
* climacteric fruits which release ethylene in an autocatalytic manner at the beginning of the maturation phase.

In these fruits, ethylene appears to initiate, coordinate and accelerate the entire physiological processes of maturation.
* Nonclimacteric fruits which do not exhibit this autocatalytic ethylene crisis at the beginning of their ripening phase, and whose maturation cannot be modified by ethylene application.

Nonclimacteric fruits are in particular citrus fruits, grapes and strawberries.

Climacteric fruits are in particular apples, pears, tomatoes, melons and bananas.

Climacteric fruits have the property, with respect to preservation, of passing very rapidly from the mature state to the overmature state following the appearance of a paroxysm of ethylene crisis.

As can be seen in FIG. 2 (curve A) for Cucumis melo, the ethylene crisis is very substantial and the fruit begins to become disorganized shortly afterwards and its market value decreases.

The present invention therefore relates to the identification of a gene complex which can be isolated from a plant cell system, characterized in that when it is transferred into a compatible cell system belonging to a plant bearing climacteric type fruits, it is expressed by conferring nonclimacteric type characteristics on the fruits.

This gene complex is more particularly useful when it is expressed in Cucumis melo.

However, it is very clear that this gene complex may also be used for transforming other climacteric fruits to nonclimacteric fruits, this being by using, more particularly, plant genetic engineering techniques.

Still more specifically, the present invention relates to a gene complex which can be isolated from a Cucumis melo type plant cell system, characterized in that when it is introduced into a plant system belonging to a plant bearing climacteric type fruits, it enables the following phenotypes, which are detectable over time and which are defined by comparison with the said unmodified cell system, to be expressed in the said cell system:
a) an ethylene release which presents a stable plateau for about 5 days,
b) a decrease in the fructose content,
c) stability of the glucose content with time,
d) a decrease in the malic acid content,
e) a substantial increase in the propionic acid content on the introduction of the gene complex into the said cell system, followed by a reversal of its variation process.

It also possesses the following characteristics:
f) a substantial increase in the total protein content,
g) a substantial increase in the fatty acid content (in the form of methyl ester) with in particular the appearance of short chain fatty acid (below C12),
h) an increase in the resistance of the flesh texture which becomes substantially more resistant to aging (in particular from maturity on).

The identification and the measurement of these various parameters will be explicitly stated in greater detail in the examples.

This gene complex is of natural origin, it was obtained by directed mutation, it is stable and self-reproducible in cell systems, in particular Cucumis melo type cell systems.

Currently, it may be reproduced according to the same method but using systems which permit rapid testing of the most promising products. In particular, this complex may be obtained from climacteric type cell systems using physical or chemical mutation methods and by selecting the products obtained by their propionic acid content.

Indeed, the complex according to the present invention confers on the products containing it, the property of possessing a high content of propionic acid which may be identified by various means, in particular by HPLC measurement. The examples will give additional information on this type of method.

When a cell system expressing this gene complex has been identified, it suffices to reproduce the cell system bearing the gene complex, which is the subject of the patent, with any cell system which is compatible or which has been made compatible. This makes it possible to obtain a novel cell system in which the gene complex is expressed.

Moreover, the gene complex according to the present invention has been introduced into the Cucumis melo line 95LS444 whose seeds have been deposited in accordance with the Budapest Treaty in the NCIMB Collection (National Collection of Industrial and Marine Bacteria-ABERDEEN AB2 1RY (Scotland-GB) 23 St. Machar Drive) on Jul. 19, 1990 under the No. 40310.

Using these seeds, the person skilled in the art can easily reproduce the invention using known techniques.

If the cell system bearing the gene complex according to the invention is reproduced with any cell system which is compatible or which has been made compatible, a cell system expressing the gene complex is obtained.

The progeny from this crossing give a segregation in which it is always possible to recover the gene complex using as screening method the specific biochemical analyses previously described and so on.

Novel stable and self-reproducible cell systems may thus be reobtained in which the gene complex of the invention is expressed.

Moreover, it is possible, as has already been achieved many times in plants, to transfer this gene complex into other cell systems, in particular by cell fusion and protoplast fusion techniques, as has already been achieved for example for obtaining cytoplasmic male sterility which was transferred from cabbage to colza.

The cell or protoplast fusion techniques will not be described in detail herein; they are known to a person skilled in the art.

Accordingly, the present invention also relates to gene complexes obtained from the *Cucumis melo* line 95LS444 deposited in the NCIMB Collection under the No. 40310.

The present invention also relates to the cells, in particular plant cells, modified by introduction of the said gene complex.

The present invention also relates to a *Cucumis melo* characterized in that:
  it exhibits a release of $C_2H_4$ of the order of not less than 10 $\mu$l kg$^{-1}$ h$^{-1}$, 7, preferably 12, days after the $C_2H_4$ release maximum,
  its propionic acid content decreases from the first to the seventh day,
  its total nitrogen content relative to the dry matter is above 1.8%,
  the percentage of γ-aminobutyric acid (GABA) relative to the total amino acids (ASP, GLU, ASN, SER, HIS, GLY, THR, ARG, ALA, TYR, GABA, MET, VAL, PHE, ILEU, LEU, ORN, LYS) is above 6%,
  the percentage C16-1 palmitoleic acid relative to the total fatty acids is above 6%,
  the percentage C18-1 oleic acid relative to the total fatty acids is below 10%,
  it contains fatty acids less than "C12".

The melon according to the present invention also contains a substantially increasing fructose level, in particular doubling from the first to the seventh day following maturation.

The examples below will make it possible to show other characteristics and advantages of the present invention.

EXAMPLE 1

The gene complex which is the subject of the present invention was obtained from cell systems consisting of *Cucumis melo* pollen.

These cell systems were subjected to various radiation according to the following procedure:
1) Determination of the radiation dose after which 50% of the cells were still alive. This radiation is generally called lethal dose 50 (LD 50).
2) Exposures of the cell systems to the LD 50.

The cell systems thus irradiated were then reproduced with compatible cell systems (derived from *Cucumis melo*).

The novel cell systems obtained were cultured and then screened so as to show the presence of the desired gene complex. The complex was screened using the decrease in the propionic acid level with time. In effect, this acid level increases with time in the original cells.

It is well known that ethylene ($C_2H_4$) is one of the factors which initiates, coordinates and accelerates the entire physiological processes of maturation of climacteric cell systems.

However, according to previous studies (De Pooter H. L., 1981; De Pooter H. L., 1982; De Pooter H. L., 1984) propionic acid might be involved as precursor and regulator of $C_2H_4$ synthesis.

This decrease in propionic acid level as a function of time was therefore chosen as confirmation of the creation of the gene complex in the cell system.

The following measurements were carried out in parallel in order to accelerate the screening procedures:
1) Evaluation of the inner texture and of the softening of the fruit as a function of time by measuring the total deformation under a 3-kg weight.
2) penetrometry at maturation (refractometric index greater than 11) for measuring the inner texture (AFNOR standard) with elimination of mean measurements below 1.5 kgf.

Thus, nonclimacteric cell systems are obtained from *Cucumis melo* which may be transferred, by crossing, in particular into related compatible systems or alternatively into other systems using molecular biology methods.

EXAMPLE 2

The object of this example is to compare the characteristics of *Cucumis melo* modified with a gene complex according to the invention (product B) to unmodified *Cucumis melo* (product A).

a) Respiratory activity and $C_2H_4$ production

*C. melo* is a climacteric fruit: a sudden increase in respiratory activity and the release of $C_2H_4$ is observed during its maturation.

The measurements of respiratory activity and $C_2H_4$ release are carried out from ripening up to senescence of the fruit. The $C_2H_4$ is assayed by gas chromatography.

Figure 1:
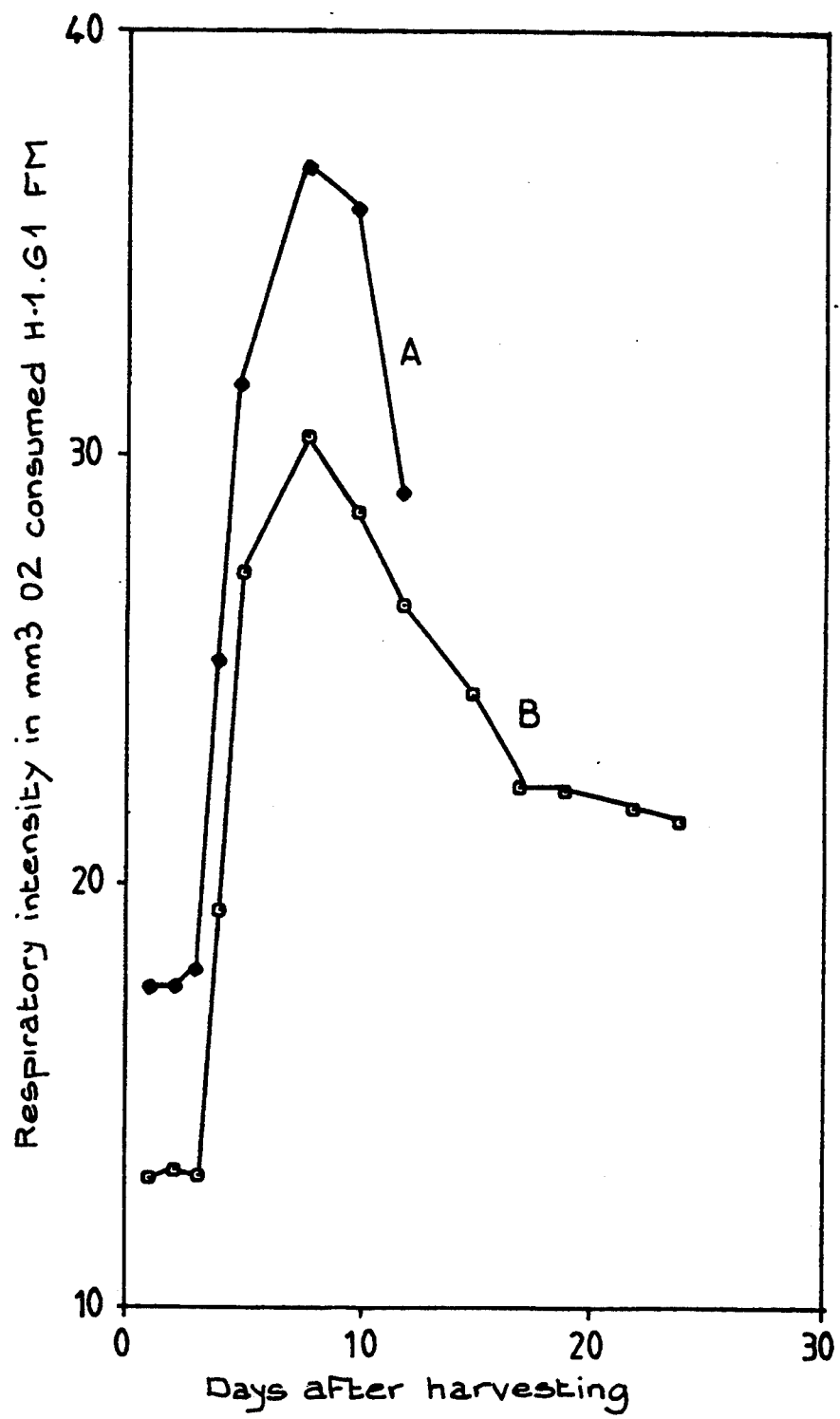
FIG. 1 represents the respiratory intensity of the control *C. melo* and *C. melo* modified according to the invention as a function of the number of days after harvesting.
Figure 2:
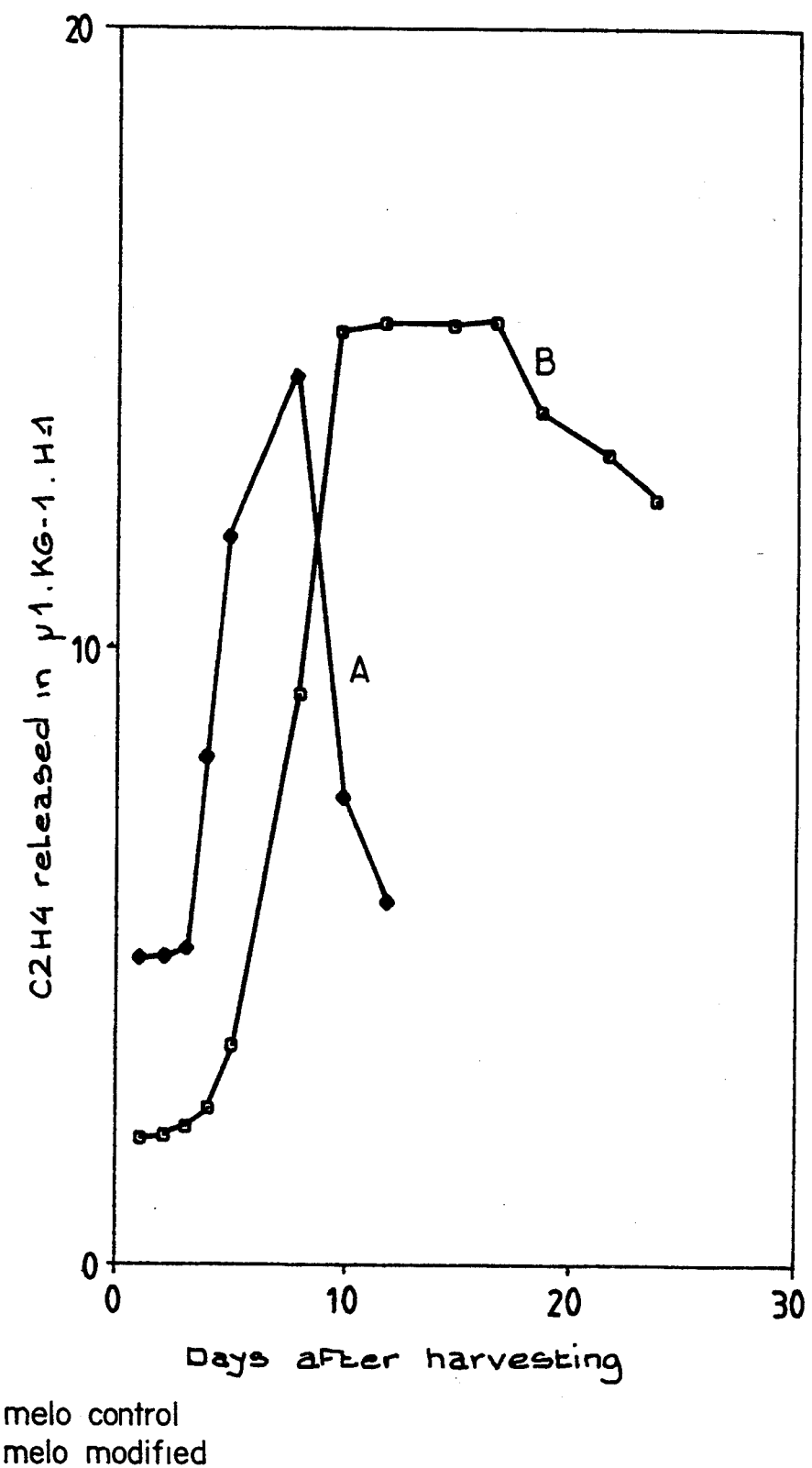
FIG. 2 represents the amount of $C_2H_4$ released for the control and the product according to the invention as a function of the number of days after harvesting.

The results represented in FIGS. 1 and 2 correspond to the mean of 6 samples.

*C. melo* according to the invention has a respiratory activity which is substantially lower than the control (FIG. 1).

A few days after harvesting, as can be seen in FIG. 2, the release of ethylene is smaller than in the modified product. The maximum amount of ethylene released is the same for the two products. This maximum release is observed 10 days later in the product of the invention.

Introduction of the gene complex transforms the ethylene peak observed for the control to a plateau which is stable for 8 days for the product according to the invention. There is thus an inactivation of the genes encoding the enzymes involved in the production of autocatalytic ethylene.

The gene complex eliminates the ethylene crisis of the cell system which thereby preserves its physiological functions for substantially longer. The cell system with climacteric reaction is transformed to a nonclimacteric cell system.

At 20° C., the maturation crisis followed by the stoppage of the physiological functions and the catabolism of the initial cell system may be characterized by the stoppage of $C_2H_4$ production.

Introduction of the gene complex allows the physiological functions to continue for about fifteen days at 20° C. after the rise in the release of $C_2H_4$.

b) Variation of carbohydrates

The reducing sugar and total sugar contents were studied at the beginning and at the end of the eating maturity phase.

This phase extends over 3 days for the product A (the assays were carried out on the first and third days).

The storage life is longest for the product of the invention (product B) (the assays were carried out on the first and seventh days).

The reducing sugars are represented mainly by fructose.

A relatively high amount of glucose is present in the control at the end of the eating maturity phase.

TABLE I

| Sugar content of the two products | | | |
|---|---|---|---|
| | | Reducing sugars g · 100 g$^{-1}$ FM | Total sugars g · 100 g$^{-1}$ FM |
| A | 1st day | 0.95 | 5.6 |
| | 3rd day | 1.5 | 6.4 |
| B | 1st day | 0.15 | 8.0 |
| | 7th day | 0.65 | 7.8 |

The results presented in Table I show that the total sugar content is higher in the product of the invention.

It should be noted that the reducing sugar content is very low in the product of the invention.

Table II shows the behavior of the cell systems before (A) and after (B) introducing the gene complex.

Introduction of the gene complex greatly reduces the initial fructose content and allows stability of the glucose content over time.

TABLE II

| | | Fructose g · 100 g$^{-1}$ FM | Glucose g · 100 g$^{-1}$ FM |
|---|---|---|---|
| A | 1st day | 0.9 | 0.05 |
| | 3rd day | 0.95 | 0.6 |
| B | 1st day | 0.1 | 0.05 |
| | 7th day | 0.65 | 0.05 | c) Variation of organic acids

The assays of organic acids by HPLC were carried out in parallel with the assays of sugars.

Table III shows the behavior of the cell systems before (A) and after (B) introducing the gene complex.

Introduction of the gene complex greatly reduces the initial malic acid content and reverses the propionic acid progression over time.

TABLE III

| | | Malic acid mg · 100 g$^{-1}$ FM | Propionic acid mg · 100 g$^{-1}$ FM |
|---|---|---|---|
| A | 1st day | 18.5 | 190 |
| | 3rd day | 11.1 | 370 |
| B | 1st day | trace | 410 |
| | 7th day | 13.9 | 270 | c) Variation of proteins

The assay of proteins, and therefore of amino acids, was performed by high performance liquid chromatography by comparisons with reference standards (e.g.: pure GABA and the like).

The results below show that the content of total amino acids, and therefore of proteins, is higher for the product of the invention (B):

Of three batches for each control species (A) and four melon batches (B) according to the invention, the assay results in an amount of 6.7 g of protein per 100 g of dry matter in the case of A and 11.0 g of protein per 100 g of dry matter for B.

Furthermore, introduction of the gene complex greatly increases the percentage of γ-aminobutyric acid (GABA) relative to the other amino acids:

A: 3.3%.
B: 7.32%.

e) Assay of total nitrogen

The assay of total nitrogen was performed on the material which was freeze-dried, then hydrolyzed for 24 hours and then passed through an automatic nitrogen analyzer.

The result shows that the introduction of the gene complex greatly increases the percentage total nitrogen relative to the dry matter:

Of five batches, a mean of 1.65% was obtained for A and 2.18% for B.

Pure nitrogen being derived from proteins, it is normal to apply a multiplier factor to this percentage of nitrogen in order to obtain a protein level. This result is consistent with paragraph d) above.

f) Variation of fatty acids

The fatty acid content was measured by means of a capillary phase column chromatograph on samples from which the oils had been extracted with hexane on the freeze-dried product.

Analysis of the fatty acids, in the form of methyl ester, of various types of melons shows that fatty acids of less than C12 exist in non-negligible amounts in the product of the invention (product B), which is very unusual.

The percentage of palmitoleic acid (C16-1) is substantially higher after introduction of the gene complex (product B) relative to the control.

The percentage of oleic acid (C18-1) decreases substantially after introduction of the gene complex.

g) Study of the texture

The melons are cut into 1-cm thick slices using a domestic slicer.

Round slices of 2.5 cm in diameter are cut out with a punch from the melon slices.

These round slices are divided into packages of 20 in 10 sachets and stored at 10° C.

This experiment was performed on melons before and after introduction of the gene complex.

The texture measurement will be performed daily (INSTRON TMSM). The pressure for breaking the structure of the samples by pressing between two plates is measured.

Figure 3:
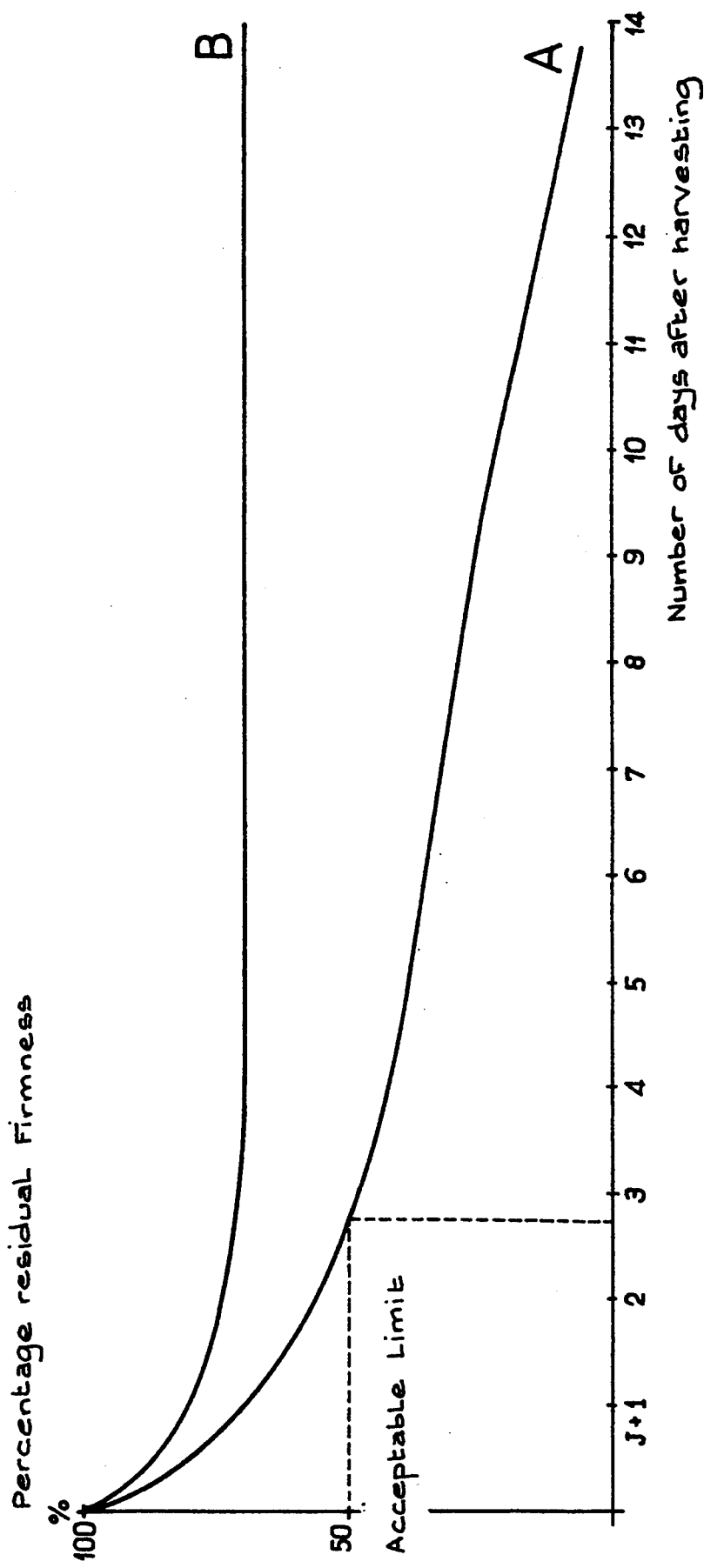
FIG. 3 represents the percentage of residual firmness for the control A and the product according to the invention B as a function of the number of days after harvesting.

The results are shown in FIG. 3 (A before introduction of the gene complex, B after introduction of the gene complex).

References

De Pooter H. L., Dirinck P. J., Willaert G. A., Schamp N. M., 1981, Phytochemistry 20, 9, 2135–2138.

De Pooter H. L., Montens J. P., Dirinck P. J., Willaert G. A., Schamp S. M., 1982, Phytochemistry 21, 5, 1015–1016.

De Pooter H. L., D'Ydewalle Y. E., Willaert G. A., Dirinck P. J., Schamp N. M., 1984, Phytochemistry 23, 1, 23–26.

We claim:

1. Cucumis melo line 95LS444.

2. Cucumis melo line according to claim 1 wherein the ethylene release presents a stable plateau for eight days after the ethylene peak.

3. Cucumis melo line according to claim 2 which exhibits an ethylene release of not less than 10 μl kg$^{-1}$ h$^{-1}$, 7 days after the ethylene release maximum.

* * * * *